United States Patent [19]

Nilsson

[11] Patent Number: 4,753,642
[45] Date of Patent: Jun. 28, 1988

[54] CONTAINER-VALVE ASSEMBLY

[76] Inventor: Leif Nilsson, Blåbärsvägen 1, S-260 40 Viken, Sweden

[21] Appl. No.: 883,621

[22] Filed: Jul. 9, 1986

[30] Foreign Application Priority Data

Jul. 19, 1985 [SE] Sweden ............................. 8503527

[51] Int. Cl.$^4$ .......................................... A61F 5/44
[52] U.S. Cl. ................................. 604/350; 128/767; 137/519; 137/533.21; 141/367; 604/323; 604/326
[58] Field of Search ........ 604/127, 317, 320, 322–326, 604/335, 347, 349, 350, 346, 254, 383; 128/760, 766, 767, 206; 4/144.1–144.4; 137/38, 41, 533.21, 533.29, 533.31, 519, 141; 383/80, 904, 906; 206/216, 364; 141/10, 68, 114, 313–317, 311 R, 367

[56] References Cited

U.S. PATENT DOCUMENTS

| 1,986,358 | 1/1935 | Rasbridge | 137/519 |
|---|---|---|---|
| 2,247,568 | 7/1941 | Armbrust | 137/519 |
| 2,554,053 | 5/1951 | Hyer | 137/519 |
| 3,299,442 | 1/1967 | White et al. | 4/144.2 |
| 3,526,227 | 9/1970 | Appelbaum | 604/350 |
| 3,535,409 | 10/1970 | Rohde | 206/605 |
| 3,928,875 | 12/1975 | Persson | 604/350 |
| 4,059,124 | 11/1977 | Hill | 137/38 |
| 4,452,253 | 6/1984 | Peterson et al. | 604/326 |
| 4,490,144 | 12/1984 | Steigerwald | 604/350 |
| 4,559,049 | 12/1985 | Haan | 604/323 |

Primary Examiner—C. Fred Rosenbaum
Assistant Examiner—Mario Costantino
Attorney, Agent, or Firm—Kane, Dalsimer, Sullivan, Kurucz, Levy, Eisele and Richard

[57] ABSTRACT

A urine-collecting container-valve assembly particularly intended for use when taking urine from the urinal bladder of a patient, particularly a bed-ridden patient. The assembly comprises a container, made of thin plastic material, having an inlet port which accommodates a non-return valve arrangement. The valve arrangement is housed in a valve housing having an inlet and an outlet. Arranged in the interior of the valve housing is a perforated plate-like element which extends transversely to the longitudinal axis of the valve housing in liquid-tight abutment with the walls of the housing. The housing also has arranged therein a pressure-activated buoyant body which is freely movable between the mutually opposing surfaces of the plate-like element and the bottom wall of the valve housing. The invention is characterized by means which co-act with the buoyant body in a manner to guide the body axially during its movement from one terminal position to another terminal position.

2 Claims, 2 Drawing Sheets

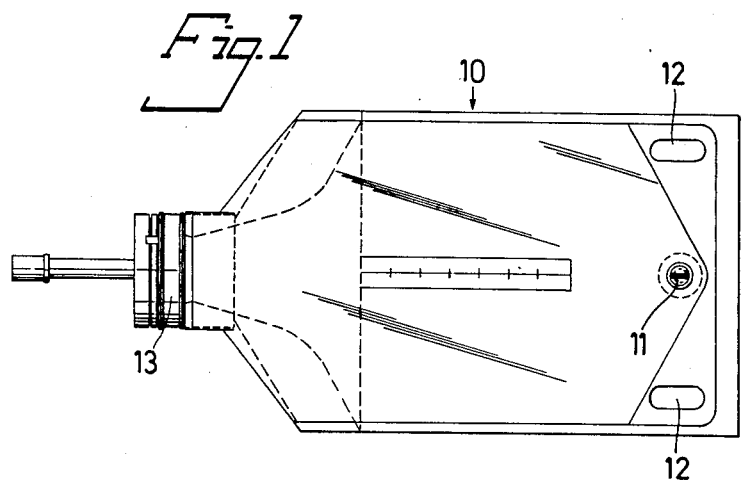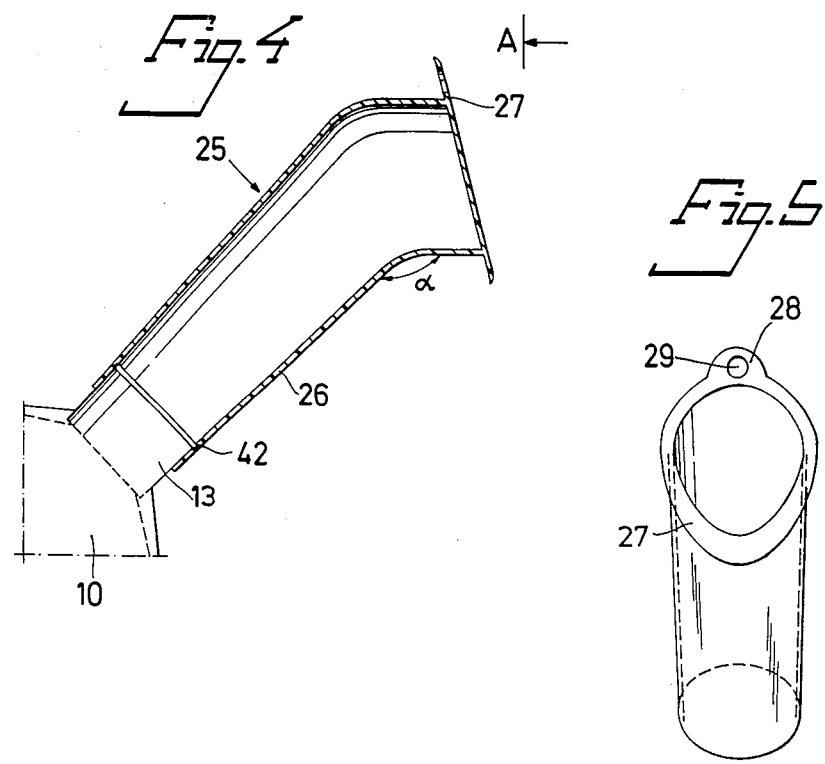

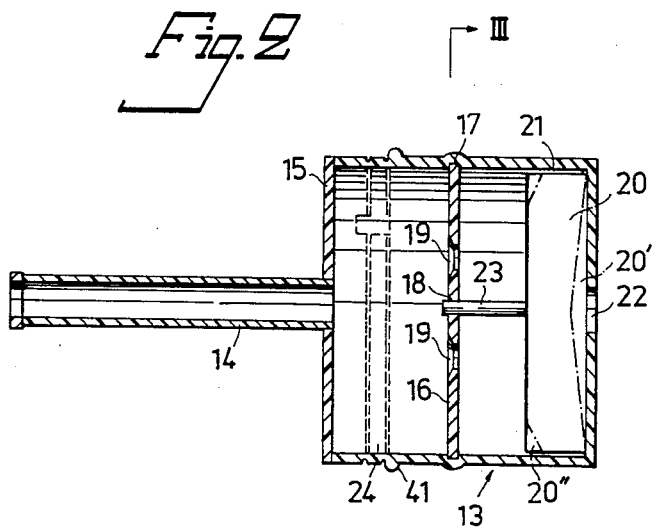
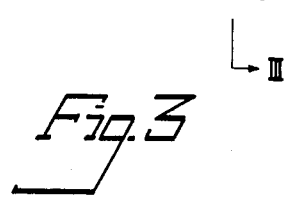
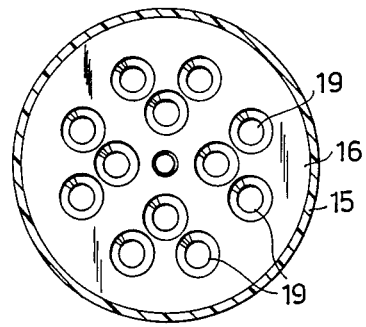

CONTAINER-VALVE ASSEMBLY

The present invention relates to a container-valve assembly, and in particular to a container-valve assembly for use when taking urine from the urinary bladder of bed-ridden patients, the container-valve assembly being of the kind which comprises a container part and a non-return valve arrangement located in an inlet port in the container part, the valve arrangement being housed in a valve housing which incorporates an inlet and an outlet and which has arranged therewithin a perforated plate-like element, the outer peripheral surfaces of which are intended to abut the opposing inner wall surfaces of the housing in a liquid-tight fashion, and in which housing there is located downstream of the plate-like element a pressure-activated buoyant body which, when activated, is free to move between the mutually opposing surfaces of the plate-like element and the downstream end of the valve housing.

A disposable container-valve assembly of this kind is known in principle from SE. No. 7302314-5. One drawback with this known container-valve assembly is that the sealing efficiency of the valve arrangement is liable to fail in the non-return mode of the valve, i.e. the valve tends to allow urine to flow in a reverse direction in a manner which can be harmful to the patient, this malfunctioning of the non-return valve being due to the fact that the buoyant body tends to become obliquely positioned in the constricted space allotted thereto, thereby allowing uring to pass beyond the buoyant body and through the perforated plate-like element.

Therefore, a prime object of the present invention is to provide a container-valve assembly of the aforementioned kind in which the non-return valve arrangement will positively prevent the backflow of urine present in the container part, while a further object is to provide a urine collecting container-valve assembly, preferably a disposable assembly, which can be produced more easily and more cheaply than prior art collecting container-valve assemblies of this kind.

A further object of the invention is to provide a novel container-valve assembly of the aforesaid kind with which the non-return valve can be connected readily both to a catheter and to a urine tube.

Still another object of the invention is to provide a novel urine tube which can be used in conjunction with the novel urine-collecting container-valve assembly therewith to create a novel system for taking urine from a patient for example.

Accordingly, this invention pertains to a urine-collecting container-valve assembly comprising a container part and a non-return valve arrangement located in an inlet port in said container part, the valve arrangement being housed in a valve housing which incorporates an inlet and an outlet and which has arranged therewithin a perforated plate-like element, the outer peripheral surfaces of which sealingly abut the opposing inner wall surfaces of the housing in a liquid-tight fashion, and in which housing there is located downstream of the plate-like element a pressure-activated buoyant body which, when activated, is free to move between the mutually opposing surfaces of the plate-like element and the downstream end of the valve housing, the container-valve assembly being characterized in that the pressure-activated buoyant body is joined with one end of a guide stem which is effective in guiding the buoyant body during movement thereof and which is freely movable in a through-opening provided in the plate-like element to an extent such that the other, free end of the guide stem is located at least within the opening when the buoyant body is located at the downstream end of the valve housing; and in that in the non-return mode of the valve arrangement the guide stem is arranged to guide the buoyant body axially into positive abutment with the plate-like element so that the surface of the buoyant body facing the plate-like element sealingly covers the perforations therein.

Thus, in the case of a container-valve assembly constructed in accordance with the invention the buoyant body incorporated in the valve arrangement is constantly guided axially during its movement between the aforesaid terminal positions, therewith to ensure effective sealing of the buoyant body against the perforated plate-like element in the non-return mode of the valve arrangement.

In order to achieve, when in use, optimal friction against the undersurface of the plate-like element, the upper surface of the buyoant body may be covered conveniently with a thin cover of material suitable in regard to the material from which the buoyant body is made.

In accordance with one advantageous embodiment of the invention, the undersurface of the buoyant body,- seen in its in-use position, is of concave configuration, so that any back-flow of urine will first fill the cavity thus presented and therewith exert an upwardly directed force on the buoyant body. The concave cavity may also be so dimensioned that when filled the upper surface of the buoyant body will lie tightly against the undersurface of the plate-like element.

So that the invention will be more readily understood and additional features of the invention and advantages afforded thereby made apparent the invention will now be described in more detail with reference to an exemplifying, preferred embodiment thereof illustrated in the accompanying schematic drawings, which also illustrate a urine tube for use in conjunction with the novel urine-collecting container-valve assembly. In the drawings, FIG. 1 illustrates a container-valve assembly according to the invention, the container part of which is preferably intended for one-time use only;

FIG. 2 is a sectional view of the valve arrangement of the assembly, the valve arrangement preferably being permanently connected to the container part; FIG. 3 is a sectional view taken on the line III—III in FIG. 2;

FIG. 4 is a longitudinal sectional view of a tubular part of the container, preferably a urine tube, which co-acts with the valve arrangement illustrated in FIGS. 2 and 3; and FIG. 5 shows the urine tube of FIG. 4 in the direction of the arrow A in FIG. 4.

In the following the container is described with reference to its in-use position, in which the container hangs generally vertically, so that all mention of top, bottom, upper and lower surfaces etc. shall be understood in respect of the container in use.

In FIG. 1 the reference 10 identifies generally a container constructed in accordance with the invention and intended for collecting urine. The container 10 of the preferred illustrative embodiment comprises a disposable urine bag, which may be graduated in a known manner to show the volumetric content of the bag, and which bag is made of some suitable synthetic material, preferably a thin plastic material. As seen in the vertical, or near vertical, in-use position of the container or bag 10, the bag has provided at the bottom thereof a plug means 11, which is preferably detachable or otherwise removable in a manner to expose a drainage orifice through which urine can be emptied or drained from the bag when the plug is removed. The bottom of the bag has a V-shaped configuration with the exit orifice and plug means 11 located generally in the apex of the V, so as to ensure that the bag 10 can be emptied completely of urine through the exit orifice when no longer blocked by the plug means. The plug means 11 may have the form of an outwardly projecting, closed spout firmly joined with the bag material, the tip of the closed spout being clipped away or cut-off when wishing to empty the bag of its liquid content. Instead of using a spout which requires cutting in order to be able to drain the contents of the bag, there may be used a spout which is initially open and held closed with the aid of a removable sealing sleeve. The bottom and/or upper portions of the urine collecting bag may be provided with one or more holes, as indicated by the reference numeral 12, which enable the bag to be hung from a suitable support means. The upper part of the urine bag merges with a conical inlet means, indicated by the reference numeral 13.

The inlet means 13 of the FIG. 1 embodiment incorporates a valve arrangement, also referenced 13, the construction of which is shown in detail in FIGS. 2 and 3, to which reference is now made.

The illustrated valve arrangement 13 incorporates a tubular pipe 14 which adjoins a circular-cylindrical, rigid valve housing 15 at one wall thereof, the pipe 14 communicating with the housing 15 substantially centrally thereof. The pipe 14 and said wall of housing 15 may, in accordance with an alternative embodiment, form a catheter unit affixed to the main body of the housing in a manner hereinafter made apparent. Arranged within the housing 15 is a plate-like element 16, the external configuration of which conforms to the transverse configuration of the housing interior, and the peripheral edges of which element engage in liquid-tight fashion in an annular groove 17 provided in the inner wall surface of the valve housing 15. The plate-like element 16 is located at approximately the midway point of the longitudinal axis of the cylindrical housing, and has a central opening 18 and a plurality of perforations 19 (FIG. 3), which in the illustrated embodiment are arranged in groups of three distributed around the opening 18 but at a given distance from the outer edge of the platelike element 16, the perforations of respective groups being of mutually the same size.

As illustrated in FIG. 2, the valve arrangement includes a pressure-activated body 20 arranged for movement between an active position, in which it sealingly abuts the perforated plate-like element in the non-return mode of the valve arrangement, and an inactive position, in which it rests against the bottom of the valve housing 15, the body 20 being made of frigolite or some other light or very light material. The peripheral surfaces of the body 20 terminate short of the inner wall surfaces of the valve housing 15, so as to leave a narrow annular gap 21, defined on one side by the inner wall surfaces of the housing. The bottom of the housing 15 has provided centrally therein an outlet opening 22. The upper surface of the body 20 is preferably firmly connected centrally thereof with one end of a guide stem 23, the other, free end of which is intended to pass freely through the central opening in the plate-like element 16.

The urine collecting bag and valve arrangement illustrated in FIGS. 1-3 may either comprise an integrated unit or the valve arrangement 13 may be detachably connected to the bag.

The urine bag-valve assembly is intended to function so that urine flows through the valve arrangement 13 and the perforations 19 in the plate-like element 16 and out onto the upper surface of the body 20, from where it passes through the annular gap 21 to the space located beneath the body and defined by the bottom wall of the housing. The urine entering the aforementioned space presses against the bottom surface of the body 20, which acts as a buoyant body, causing the body to be lifted towards the central opening 18 while guided positively by the guide stem 23. The urine flows from the space into the bag 10, through the outlet opening 22.

The aforedescribed valve arrangement functions as a non-return valve, or check valve, when a bag which is full or partially filled with urine is handled, for some reason or other, in a manner which causes the urine enclosed in the bag to run back through the bag inlet, in which case the back flow of urine impinges on the bottom surface of the body 20 and forces it into sealing abutment with the undersurface of the plate-like element 16, therewith blocking entrance to the through passage 18 and perforations 19 in the element 16.

In order to ensure good frictional contact with the undersurface of the plate-like element 16, therewith to seal effectively against the perforations 19 in the non-return mode of the valve arrangement, the upper surface of the body 20 is preferably covered with a layer of material suitable to this end, e.g. a thin covering of plastic material (indicated by reference numeral 40), the choice of material used in this regard being conditioned by the material from which the body 20 is made. As with the illustrated embodiment of FIG. 2, the undersurface of the body 20 is preferably concave in shape, so as to ensure upward movement of the buoyant body 20 when subjected to back pressure, optionally to an extent such that the upper surface of the body is brought into contact with the undersurface of the plate-like element 16 prior to urine attempting to pass upwards through the annular gap 21. In order to ensure that urine entering the valve housing 16 will flow positively towards the annular gap 21, the upper surface edges of the body 20 may be bevelled (as shown at 20'') this bevelled surface extending from the outer peripheral edge of the body 20 to the region of said body which lies in register axially with the region in which the perforations 19 terminate outwardly.

As illustrated in broken lines in FIG. 2, and as indicated in the aforegoing, the pipe 14 and the housing wall to which the pipe is connected may form a detachable catherer unit, which is held to the main body of the rigid housing 15 by means of a peripherally extending tear-strip 24, which when torn away allows the catheter portion to be removed so as to expose the interior of the remainder of the valve housing 15.

Thus, removal of the catheter unit in this particular embodiment of the valve arrangement 13 with the aid of the connecting tear-strip 24 enables the valve arrangement to be modified readily for use with a urine tube, one end of the tube being connected to the open end of the housing 15 in a manner hereinafter described with reference to FIG. 4. Although when used to collect urine the illustrated and described container and its associated valve arrangement is primarily intended for one-time use only, it will be understood that when used to collect liquids other than urine the container-valve assembly may be used a number of times when no hazard is incurred in so doing.

FIGS. 4 and 5 illustrate a urine tube which is formed particularly for use with the urine container-valve assembly 10,13 described and illustrated with reference to FIGS. 1-3.

FIG. 4 is a longitudinal view in section of a tubular urine tube 25 having a conical lower part 26, the mouth of which is shaped and dimensioned to fit snugly around and co-act with the end part of the valve housing 15 exposed when removing the tear-off joining strip 24. To this end, the valve housing 15 is provided with an external peripheral bead or like promontory 41 (vide Fiqure 2) which when connecting the valve housing (and also the urine collecting bag) to the urine tube enters a peripheral groove 42 located in the region of the narrower end of the tube 25, so that the valve arrangement is connected in liquid-tight fashion to the conical part 26 of the tube 25.

The opposite end of the urine tube 25 is bent to an obtuse angle α and has an oval shaped orifice surrounded by a flange 27, the edge portions of which are bent slightly downwards. The flange 27 has a semi-circular lug 28 which incorporates a hole 29 by means of which the urine tube 25 can be hung on a suitable support.

The novel urine tube, which is made from a synthetic material suitable for the purpose intended, is meant for one-time use only and can be used by both male and female patients. The flange 27 is made of a soft resilient material, friendly to the skin, and in the case of a female patient is inserted into the vagina and seals against the wall thereof, whereas in the case of a male patient the patient's penis is inserted into the upper, bent portion of the tube. The urine tube connects in both instances with the urine collecting bag and the valve arrangement in the aforedescribed manner. The novel urine tube may alternately be made of a plastically deformable material.

The urine-collecting container-assembly proposed in accordance with the invention provides a totally novel instrument for relieving the urinary bladder of a bedridden patient for example, this instrument being capable of use in conjunction with a catheter or with a urine tube, thus opening new possibilities for facilitating the emptying of the urinary bladder of different categories of patient.

It will be understood that the pressure-activated buyoant body 20 can be guided axially in the valve housing 15 with the aid of more than one guide stem, if so desired.

I claim:

1. A urine-collecting container-assembly comprising container means having an inlet port having an inner wall, wherein a non-return valving means is arranged within said inlet port, wherein said valving means comprises a first plate-like member having perforations, a downstream surface, and outer peripheral surfaces which sealingly abut the inner wall of the inlet port, a second plate-like member is arranged in the inlet port downstream of the first plate-like member and proximal to the container means, said second plate-like member has outer peripheral surfaces which sealingly abut the inner wall of the inlet port and have an opening therein, a buoyant member having an upstream surface, a lateral surface, and a concave downstream surface is arranged between said first plate-like member and said second plate-like member, the upstream surface of said buoyant member is attached to a guide stem member which is freely movable in an opening in said first plate-like member, outer edges of the upstream surface are beveled in the downstream direction, the guide stem is arranged so that when the buoyant member moves axially against the downstream surface of said first plate-like member, the perforations in said first plate-like member are sealed, the lateral surface of the buoyant member is spaced from the inner wall of the inlet port so that fluid may pass therebetween, and the upstream surface of the buoyant member has a thin plastic sealing layer thereon; and wherein said inlet port has a catheter connection member attached therein by a circumferentially extending tear-off strip, said catheter connection having a distal member suitable for direct connection to a catheter and the portion of the inlet port proximal to said tear-off strip comprising means for locking engagement with corresponding locking means of one end of a urine tube.

2. The container-valve assembly of claim 1, wherein the urine tube defines a lumen and has proximal and distal ends, the proximal end having locking means suitable for connection to said inlet port and said distal end being bent at an obtuse angle and having a flange arranged circumferentially, said flange being made of soft, pliable material.

* * * * *